(12) United States Patent
Fascina et al.

(10) Patent No.: US 9,168,211 B2
(45) Date of Patent: Oct. 27, 2015

(54) METHOD OF MAKING AN ANHYDROUS, PIGMENTED COMPOSITION

(71) Applicant: JOHNSON & JOHNSON CONSUMER INC., Skillman, NJ (US)

(72) Inventors: Luna Fascina, Valinhos/SP (BR); Danielle Lima Lorenzetti, Villa Branca-Jacarei/SP (BR); Maria Emilia de Oliveira Brenha Ribeiro, Sao Jose dos Campos-SP (BR); Rodrigo Collina Romanhole, Villa Branca-Jacarei/SP (BR)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

(21) Appl. No.: 14/228,745

(22) Filed: Mar. 28, 2014

(65) Prior Publication Data

US 2015/0272841 A1  Oct. 1, 2015

(51) Int. Cl.
| | | |
|---|---|---|
| *A61K 8/00* | (2006.01) | |
| *A61K 8/25* | (2006.01) | |
| *A61Q 17/04* | (2006.01) | |
| *A61Q 1/02* | (2006.01) | |
| *A61K 8/891* | (2006.01) | |
| *A61K 8/19* | (2006.01) | |
| *A61K 8/37* | (2006.01) | |

(52) U.S. Cl.
CPC ... *A61K 8/25* (2013.01); *A61K 8/19* (2013.01); *A61K 8/37* (2013.01); *A61K 8/891* (2013.01); *A61Q 1/02* (2013.01); *A61Q 17/04* (2013.01); *A61K 2800/592* (2013.01)

(58) Field of Classification Search
None
See application file for complete search history.

(56) References Cited

U.S. PATENT DOCUMENTS

| | | | | |
|---|---|---|---|---|
| 6,379,680 | B2 * | 4/2002 | Gers-Barlag et al. | 424/401 |
| 6,521,240 | B1 * | 2/2003 | Minerath, III | A61K 8/02 424/400 |
| 6,558,683 | B2 * | 5/2003 | Gers-Barlag et al. | 424/401 |
| 7,030,985 | B2 * | 4/2006 | Jager-Lezer et al. | 356/402 |
| 7,056,496 | B2 | 6/2006 | Pate et al. | |
| 7,314,612 | B2 * | 1/2008 | Ferrari et al. | 424/78.08 |
| 7,887,785 | B2 | 2/2011 | Rojas-Wahl et al. | |
| 2003/0017184 | A1 * | 1/2003 | Gers-Barlag et al. | 424/401 |
| 2004/0076594 | A1 * | 4/2004 | Legrand | A61K 8/22 424/62 |
| 2006/0246027 | A1 * | 11/2006 | Tanner | A61K 8/0212 424/70.12 |
| 2007/0009456 | A1 * | 1/2007 | Delacour et al. | 424/63 |
| 2007/0189989 | A1 | 8/2007 | Cantwell et al. | |
| 2007/0297997 | A1 | 12/2007 | Tanner | |
| 2008/0213593 | A1 | 9/2008 | Subramaniam et al. | |
| 2008/0226575 | A1 * | 9/2008 | Hanna | A61K 8/817 424/70.7 |
| 2009/0257966 | A1 | 10/2009 | Schlossman et al. | |
| 2009/0270298 | A1 * | 10/2009 | Compain | A61K 8/368 510/136 |
| 2010/0087394 | A1 * | 4/2010 | Twydell | A61K 8/042 514/63 |
| 2010/0278922 | A1 * | 11/2010 | Vol | A61K 38/23 424/489 |
| 2011/0293543 | A1 | 12/2011 | Yu | |
| 2012/0100216 | A1 * | 4/2012 | Vol | A61K 9/0095 424/484 |
| 2014/0242016 | A1 * | 8/2014 | Binks et al. | 424/68 |

FOREIGN PATENT DOCUMENTS

| | | |
|---|---|---|
| EP | 1608331 | 12/2005 |
| FR | 2930435 A1 | 8/2010 |

\* cited by examiner

*Primary Examiner* — Robert A Wax
*Assistant Examiner* — Olga V Tcherkasskaya

(57) ABSTRACT

The invention relates to a method of making an anhydrous, pigmented sunscreen composition. The method comprises first adding a hydrophobic silica to a lipid phase comprising a dispersed color pigment and an organic UV-filter and homogenizing the mixture. Next, a hydrophilic silica is added and re-homogenization is performed.

6 Claims, No Drawings

METHOD OF MAKING AN ANHYDROUS, PIGMENTED COMPOSITION

FIELD OF THE INVENTION

The present invention relates to methods of making an anhydrous, pigmented composition and, in particular, to methods of making anhydrous, pigmented compositions comprising organic ultraviolet (UV) filters.

BACKGROUND OF THE INVENTION

Various personal care products are known to be useful for treating the skin. For example, color cosmetics are known for imparting color to the skin and sunscreen compositions that include UV filters are known for protecting the skin from harmful UV-radiation.

However, the inventors of the instant invention have found that combining color pigments with organic UV-filters creates a complex formulation that is not easy to stabilize. The inventors have found that a particular series of method steps involving the use of hydrophobic and hydrophilic silica surprisingly solves the problems of phase stability. While the use of hydrophobic and hydrophilic silica in sunscreen compositions is known (for example, EP1608331, entitled "Sunscreen Composition Comprising A Mixture of Silicas," discloses sunscreens that are formulated in the form of a transparent gel and include a mixture of hydrophobic and hydrophilic silicas), the prior art does not teach or suggest the method steps of the instant invention.

SUMMARY OF THE INVENTION

The invention relates to a method of making an anhydrous, pigmented sunscreen composition, comprising in sequence: adding a hydrophobic silica to a lipid phase comprising a dispersed color pigment and an organic UV-filter; homogenizing the lipid phase comprising the hydrophobic silica by rotary mixing at a rotation speed of at least 1000 rpm; adding a hydrophilic silica to the lipid phase comprising hydrophobic silica; and re-homogenizing the lipid phase comprising the hydrophobic silica and the hydrophilic silica by rotary mixing at a rotation speed of at least 1000 rpm.

DETAILED DESCRIPTION OF THE INVENTION

As described above, it has been discovered that an anhydrous composition including color pigments and organic UV-filters can be made phase stable using a method that includes the steps of adding a hydrophobic silica to a lipid phase and subsequently adding a hydrophilic silica. The inventors have found that using techniques described herein, it is furthermore surprisingly possible to stabilize such compositions that include not only very high levels of oil, but also substantial levels of particulates including silicone elastomers.

Unless defined otherwise, all technical and scientific terms used herein have the meaning commonly understood by one of ordinary skill in the art to which the invention pertains. All publications, patent applications, patents, and other references mentioned herein are incorporated by reference. Unless otherwise indicated, a percentage refers to a percentage by weight (i.e., %(W/W)).

As used herein, "cosmetically-acceptable" means suitable for use in topical contact with tissues (e.g., the skin) without undue toxicity, incompatibility, instability, irritation, allergic response, or the like. This term is not intended to limit the composition it describes as for use solely as a cosmetic (e.g., the composition may be used as a pharmaceutical).

As used herein, "substantially free" means the composition contains less than about 1, such as less than about 0.1, e.g., less than about 0.01 weight percent of an ingredient. Furthermore, "anhydrous" means substantially free of water.

"Particulate" means a finely divided material that is generally solid at room temperature and insoluble in the vehicle of the composition. Particulates are generally suspended or dispersed in the composition by means of, e.g., steric (electrical) forces and/or by buoyancy forces due to a sufficiently high viscosity or yield stress of the phase in which the particulate is dispersed or suspended. Particulates do not appreciably dissolve in the composition, typically having an average particle size of greater than about 0.1 microns. Non-limiting examples of particulates include pigments such as color pigments, filler pigments; polymeric particulates (e.g., nylon and the like), particulate biological actives, silicone elastomers among other particulates. According to certain embodiments of the invention, compositions of the present invention include from about 10% to about 50% by weight, such as from about 20% to about 40%, such as from about 25% to about 35% of particulates.

In particular, compositions of the present invention are pigmented and therefore include one or more pigments, and, in particular, one or more color pigments. "Color pigment", means a pigment that imparts a color (other than white). The color pigment may be an inorganic color pigment, a lake pigment, or an interference pigment. The total amount of color pigment may range from about 0.2% to about 2%, such as from about 0.5% to about 1.5%. In one notable embodiment, the color pigment is an inorganic color pigment. In another embodiment, the color pigment consists essentially of inorganic color pigments (i.e., the composition is substantially free of lake pigments and interference pigments). Inorganic color pigments, lake pigments and interference pigments are discussed below.

Inorganic color pigments include iron oxides, including colored oxide or oxyhydroxide or hydroxide pigments such as red and yellow iron oxides, ultramarine and chromium or chromium hydroxide, manganese oxides, brown or red clays (e.g., phylosilicate) pigments and mixtures thereof. In one embodiment, the color pigment includes iron oxide. In one embodiment, the color pigment is at least 50% iron oxide. Specific examples of suitable inorganic color pigments include iron oxide dispersed in a carrier of isononyl isononanoate, isopropyl myristate, and stearalkonium hectorite commercially available as INBP75EB, INBP75ER, and INBP55EY from Kobo of South Plainfield N.J.

Examples of lake pigments include organic dyes such as azo, indigoid, triphenylmethane, anthraquinone, and xanthine dyes that are designated as D&C and FD&C blues, browns, greens, oranges, reds, yellows, etc., precipitated onto inert binders such as insoluble salts. In one embodiment, the lake pigment is selected from Red 6, Red 7, Yellow 5 and Blue #1.

Examples of interference pigments include those containing mica substrates, bismuth oxychloride substrates, and silica substrates, for instance mica/bismuth oxychloride/iron oxide pigments, titanium dioxide and/or iron oxides coated onto mica, mica/titanium dioxide/iron oxide pigments and borosilicate-containing pigments.

The present compositions also comprise a hydrophobic silica and a hydrophilic silica, which are added to the composition in a particular order. The inventors have found that these two filler pigments are critically important for the phase stability of the composition. In certain embodiments, either or both the hydrophobic silica and hydrophilic silica have a bulk density of about 1.9 to about 2.4 g/cc. In one embodiment, the silicas are at least about 80% by atomic weight, such as at least about 90% by atomic weight, such as at least 95% by atomic weight silicon and oxygen.

The hydrophobic silica is a silica particulate having a hydrophobic surface. Suitable examples are silica coated with a hydrophobically functional silane or a long chain hydrocarbon (e.g., $C_{12}$ or greater). One suitable example is HDK H20, a pyrogenic silica particulate coated with dimethyl siloxy functional groups (also known as silica dimethyl silylate) having a Brunauer-Emmett-Teller ("BET") surface area of 170-230 $m^2$/g and a bulk density of about 2.2 g/cc, and a tamped density of about 40 g/L, available from Wacker Chemie AG of Munich, Germany.

The hydrophilic silica is not treated or coated with hydrophobic material and, as such, generally has a hydrophilic surface. One suitable example is HDK N20, a pyrogenic silica particulate having a BET surface area of 175-225 $m^2$/g and a tamped density of about 40 g/L, available from Wacker Chemie AG of Munich, Germany.

Furthermore, compositions of the present invention may include other filler pigments to provide opacity or other functionality but not color, and as one skilled in the art will readily recognize. Suitable filler pigments include titanium dioxide, talc, mica, silica, boron nitride, white clays (e.g., kaolin/china clay). The average particle size of the filler pigments may range from about 0.5 microns to about 20 microns. The filler pigments may be present in the composition in a concentration from about 5% to about 35%, such as from about 10% to about 25%.

Specific examples of suitable filler pigments include titanium dioxide such as may be dispersed in a carrier of isononyl isononanoate, isopropyl myristate, stearalkonium hectorite, and isopropyl titanium available as INBP70U from Kobo of South Plainfield N.J.; mica (available as Serecite PHN from Presperse Incorporated of Somerset N.J.); boron nitride, among other fillers.

The compositions of the present invention are anhydrous and therefore comprise a lipid phase. The lipid phase includes one or more hydrophobic compounds that are co-solublized. Hydrophobic compounds are generally water insoluble and may be selected to meet one or more of the following four criteria: (a) has a carbon chain of at least four carbons in which none of the four carbons is a carbonyl carbon; (b) has two or more, such as up to about 500 alkyl siloxy groups; (c) has two or more oxypropylene groups in sequence; or (d) is an organic UV filter that satisfies (a), (b), or (c). The hydrophobic compounds may include linear, cyclic, aromatic, saturated or unsaturated groups. According to certain embodiments, compounds that are amphiphilic are excluded from the definition of "hydrophobic compounds" and such, compounds that have hydrophilic moieties, such as anionic, cationic, zwitterionic, or nonionic groups, that are polar, including sulfate, sulfonate, carboxylate, phosphate, phosphonates, ammonium, including mono-, di-, and trialkylammonium species, pyridinium, imidazolinium, amidinium, poly(ethyleneiminium), ammonioalkylsulfonate, ammonioalkylcarboxylate, amphoacetate, and poly(ethyleneoxy)sulfonyl moieties, are so excluded.

The lipid phase may include one or more oils. By "oils," it is meant hydrophobic compounds that are liquid at 25° C. Suitable oils include those that do not appreciably absorb UV-radiation such as various hydrocarbons (straight or branched chain alkanes or alkenes, ketone, diketone, primary or secondary alcohols, aldehydes, sterol esters, alkanoic acids, turpenes, monoesters), such as those having a carbon chain length ranging from $C_6$-$C_{38}$, such as $C_6$-$C_{18}$. Other oils include liquid organic-UV filters described below. As described above, the inventors have found that using techniques described herein it is possible to stabilize compositions having very high levels of oil. As such, according to certain embodiments of the invention, the concentration of oil in the composition is from about 45% to about 75%, such as from about 45% to about 60%.

Specific non-limiting examples include emollient cosmetic oils including, without limitation, esters such as isopropyl palmitate, isopropyl myristate, isononyl isonanoate (such as WICKENOL 151 available from Alzo Inc. of Sayreville, N.J.), $C_{12}$-$C_{15}$ alkyl benzoates (such as FINSOLV TN from Innospec Active Chemicals), caprylic/capric triglycerides, silicone oils (such as dimethicone and cyclopentasiloxane), pentaerythritol tetraoctanoate, mineral oil, dipropylene glycol dibenzoate, PPG-15 stearyl ether benzoate, PPG-2-Myristyl Ether Propionate, ethyl methicone, diethylhexylcyclohexane. Further examples of oils include other functional oils such as vitamin E acetate, among other functional oils. Other suitable oils include liquid, organic UV-filters such as esters of cinnamonic acid, in particular ethylhexyl methoxycinnamate, 4-methoxycinnamonic acid-2-ethylhexylester, 4-methoxycinnamonicacid propylester, 4-methoxycinnamic acid isoamyl ester, 2-cyano-3,3-phenylcinnamonic acid-2-ethylhexyl ester (octocrylene); esters of salicylic acid, i.e., salicylic acid-2-ethylhexylester, salicylic acid-4-isopropylbenzyl ester, salicylic acid homomenthyl ester, and 3,3,5-Trimethylcyclohexyl 2-hydroxybenzoate (homosalate).

In certain embodiments, the lipid phase further includes a wax. By wax, it is meant one or more hydrophobic compounds that have a melting point (or melting range) that is in the range from 30° C. to 75° C. and do not meet the definition of UV-filter, defined previously. Suitable waxes include any of various hydrocarbons (straight or branched chain alkanes or alkenes, ketone, diketone, primary or secondary alcohols, aldehydes, sterol esters, alkanoic acids, turpenes, monoesters), such as those having a carbon chain length ranging from $C_{12}$-$C_{38}$. Also suitable are diesters or other branched hydrocarbon esters and silicone waxes. In one embodiment, the compound is an ester of an alcohol (glycerol or other than glycerol including diesters or other branched esters) and a $C_{18}$ or greater fatty acid. Non-limiting examples include any of various natural waxes including shea (*Butyrospermum parkii*) butter, lotus wax; beeswax, insect waxes, sperm whale oil, lanolin, vegetable waxes such as canauba wax, jojoba oil, candelilla wax; mineral waxes such as paraffin wax; and synthetic waxes such as cetyl palmitate, lauryl palmitate, cetostearyl stearate, and polyethylene wax; and silicone waxes such as $C_{30-45}$ Alkyl Methicone; and $C_{3045}$ Olefin (e.g., Dow Corning AMS-C30, having a melting point of 70° C., available from Dow Corning of Midland, Mich.). In certain embodiments, the wax component includes a high melting point ester of glycerol such as glycerol monostearate. The amount of wax may be present in the composition from about 0.1% to about 5%, or from about 0.1% to about 2%. According to certain embodiments, the concentration of wax is less than about 1% by weight.

In order to provide protection from UV radiation, the lipid phase includes one or more organic UV-filters. Organic UV-filters suitable for use in compositions of the present invention are cosmetically-acceptable compounds that absorb radiation in the UV range, are solid at ambient temperature (22° C.) and pressure (1 atmosphere), and are generally soluble in one or more organic hydrocarbon solvents. The organic UV filter absorbs radiation in some portion of the ultraviolet spectrum (290 nm-400 nm), and may have an extinction coefficient of about 1000 mol$^{-1}$ cm$^{-1}$ or more, for example greater than 10,000 or 100,000 or 1,000,000 mol$^{-1}$ cm$^{-1}$, for at least one wavelength within the above-defined ultraviolet spectrum. Compositions of the present invention include a dissolved, solid, organic UV filter. Solid, organic UV-filters that are useful in the present invention are cosmetically-acceptable compounds that absorb radiation in the UV range, are solid at ambient temperature (22° C.) and pressure (1 atmosphere), and are generally soluble in one or more organic hydrocarbon solvents. The organic, UV filter absorbs radiation in some portion of the ultraviolet spectrum (290 nm-400 nm), and may have an extinction coefficient of about 1000 mol$^{-1}$ cm$^{-1}$ or more, for example greater than 10,000 or 100,000 or 1,000,000 mol$^{-1}$ cm$^{-1}$, for at least one wavelength within the above-defined ultraviolet spectrum. The organic UV-filter, which is solid at ambient temperature, is dissolved and homogeneously distributed in the composition (exclusive of any propellant).

Organic UV-filters that dissolve in the lipid phase include benzophenone-3 (i.e., oxybenzone), 2-Hydroxy-4-methoxyphenyl)-(2-hydroxyphenyl)methanone (i.e., dioxybenzone), 2-(2H-Benzotriazol-2-yl)-4-methylphenol, also known as drometrizole trisiloxane (also known as MEXORYL XL from L'Oreal SA), butylmethoxy dibenzoylmethane ("avobenzone"), 4-methyl benzilidene camphor ("4-MBC"), ethylhexyl triazone (available as UVINUL T-150 from BASF of Ludwigshafen, Germany), diethylamino hydroxybenzoyl hexyl benzoate ("DHHB") available as UVINUL A Plus from BASF; and Bemotrizinol (available as TINOSORB S from BASF), Menthyl-2-aminobenzoate ("menthyl anthranilate"), 4-Aminobenzoic acid ("PABA"), hydroxy methylphenyl benzotriazole, and dimethicodiethyl benzal malonate, and combinations thereof. Other suitable UV-filters include those that are liquid under ambient conditions, such as those described above.

The total concentration of organic UV-filters may be from about 3% to about 25%, such as from about 5% to about 20%, such as from about 10% to about 18% by weight of the composition.

According to certain embodiments, compositions of the present invention include a silicone elastomer. "Silicone elastomer", means chemically or physically crosslinked molecules having at least one siloxane repeat unit, wherein the material is generally flexible and deformable and having a modulus of elasticity such that the material is resistant to deformation and has a limited ability to expand and to contract. The material is capable of returning to its original shape after it has been stretched. Silicone elastomers are formed of polymeric chains of high molecular weight, the mobility of which is limited by a uniform network of crosslinking points. The silicone elastomer may either be an emulsifying or non-emulsifying crosslinked organopolysiloxane elastomer or combinations thereof.

The term "non-emulsifying," as used herein, defines crosslinked organopolysiloxane elastomer from which hydrophilic groups such as polyoxyalkylene units are absent. As such, they are not amphiphilic. Examples of particularly suitable silicone elastomers are organopolysiloxanes available under the INCI names of dimethicone/vinyl dimethicone crosspolymer, dimethicone crosspolymer, dimethicone/cetearyl dimethicone crosspolymer, and dimethicone/bis-isobutyl PPG-20 crosspolymer. Other examples of non-emulsifying silicone elastomers include Dimethicone/Vinyl Dimethicone Crosspolymers sold as KSG 1610 and USG 107A, both from Shin-Etsu of Japan). Ordinarily these materials are provided as a 1-30% crosslinked silicone elastomer dissolved or suspended in a dimethicone fluid (usually cyclomethicone). For purposes of definition "crosslinked silicone elastomer" refers to the elastomer alone rather than the total commercial compositions which also include a solvent (e.g. dimethicone) carrier.

An example of a dimethicone/vinyl dimethicone crosspolymers is available as Dow Corning 9701 Cosmetic Powder from Dow Corning of Midland, Mich. An example of a dimethicone/bis-isobutyl PPG-20 crosspolymer is available as Dow Corning EL-8050 ID also from Dow Corning. An example of a dimethicone/cetearyl dimethicone crosspolymer is available as VELVESIL DM from Momentive Specialty Chemicals Inc. of Waterford, N.Y.

The silicone elastomers of the present invention may range in concentration from about 0.1 to about 30%, preferably from about 0.5% to about 30%, such as from about 2% to about 25% by weight of the cosmetic composition. As discussed above, methods of the present invention may be used to stabilize compositions having high levels of silicone elastomer. As such, according to certain embodiments, the concentration of silicone elastomer is greater than about 8%, such as from about 8% to about 20%, by weight of the total weight of the composition.

According to another embodiment, the silicone elastomer and all waxes are present in a weight ratio of at least about 8:1, such as at least about 12:1, such as about 12:1 to about 100:1. Weights of silicone elastomer exclude any solvent such as cyclomethicone found in commercial "elastomer" silicones. For instance, the concentration of silicone elastomer in VELVESIL DM is believed to be between about 10% and 30% by weight and the concentration of silicone elastomer in DOW CORNING EL-8050 ID is believed to be between about 15% by weight, whereas Dow Corning 9701 Cosmetic Powder is about 100% silicone elastomer.

Compositions of the present invention may include a film-forming polymer to enhance film formation and provide some water resistance. "Film-forming polymer", means a polymer that, when dissolved in the composition, permits a continuous or semi-continuous film to be formed when the composition is spread onto, e.g., smooth glass, and the liquid vehicle is allowed to evaporate. As such, the polymer should dry on the glass in a manner in which it should be predominantly continuous over the area upon which it is spread, rather than forming a plurality of discrete, island-like structures. Generally, the films formed by applying compositions on the skin according to embodiments of the invention described herein, are less than, on average, about 100 microns in thickness, such as less than about 50 microns.

Suitable film-forming polymers include natural polymers such as polysaccharides or proteins and synthetic polymers such as polyesters, polyacrylics, polyurethanes, vinyl polymers, polysulfonates, polyureas, polyoxazolines, and the like. Specific examples of film-forming polymers include, for example, acrylic homopolymers or copolymers with hydrophobic groups, such as acrylate/octylacrylamide copolymers, including DERMACRYL 79, available from Akzo Chemical of Bridgewater, N.J.; dimethicone/acrylates dimethicone copolymer, available as X-22-8247D from Shin-Etsu of Japan; hydrogenated dimer dilinoleyl/dimethylcarbonate copolymer, available from Cognis Corporation of Ambler, Pa. as COSMEDIA DC; copolymer of vinylpyrrolidone and a long-chain alpha-olefin, such as those commercially available from ISP Specialty Chemicals of Wayne, N.J. as GANEX V220; vinylpyrrolidone/tricontanyl copolymers available as GANEX WP660 also from ISP; water-dispersible polyesters, including sulfopolyesters such those commercially available from Eastman Chemical as EASTMAN AQ 38S. One particularly suitable film-forming polymer is a hydrogenated polycyclopentadiene, such as is commercially available in isododecane as KOBOGUARD 5400 IDD from Kobo Products Inc. of South Plainfield, N.J.

The amount of film-forming polymer present in the composition may be from about 0.25% to about 15%, or from about 0.5% to about 10%, or from about 1% to about 5%, by weight of the composition.

In one embodiment, the composition comprises an additional active agent. As used herein, "additional active agent" means a compound (e.g., synthetic or natural) that provides a cosmetic or therapeutic effect on the skin, such as a therapeutic drug or cosmetic agent. Examples of therapeutic drugs include small molecules, peptides, proteins, anti-aging agents, anti-inflammatory agents, anti-acne agents, antimicrobial agents, antioxidants, vitamins and skin lightening agents. The amount of the additional active agent in the composition will depend on the active agent, other ingredients present in the composition, and the desired benefits of the composition. In one embodiment, the composition contains a safe and effective amount of the additional active agent, for example, from about 0.001 percent to about 20 percent, by weight, such as from about 0.01 percent to about 10 percent, by weight, of the composition.

Other optional ingredients include abrasives, absorbents, aesthetic components such as, humectants, bulking agents, cosmetic biocides/preservatives. According to certain embodiments, to promote stability and aesthetics, compositions of the present invention are substantially free of certain ingredients such as one or both of $C_2$-$C_3$ mono-alcohols (e.g., ethanol, isopropanol) and/or glycols (e.g., propylene glycol, butylenes glycol, and hexylene glycol).

Compositions of the present invention are typically color cosmetics and are for application to the skin, especially the face, but compositions of the present invention may be applied to the body as well. Compositions of the present invention may be in the form of a mousse or paste.

Process of Making

The inventors have found that surprisingly phase stable, anhydrous compositions that include organic UV-filters and color pigments can be formed. The organic UV filter may include a combination of solid UV-filters and liquid UV-filters. The lipid phase of the compositions may further include other hydrophobic compounds such as oils, waxes, preservatives, antioxidants, vitamins, preservatives and the like.

According to one embodiment, prior to adding the hydrophobic silica the lipid phase is heated to a temperature sufficient to render the lipid phase fluid (e.g. melted) and is mixed. Additionally, the lipid phase may then be cooled and color pigments added thereto, and the lipid phase may be mixed to a high degree of homogeneity, such as using a rotary mixer at high speed, for example at least 1000 rpm (herein after also referred to as "homogenized under high shear mixing"). The rotation may be accomplished using, for example, a shearing element that contacts or is immersed in the lipid phase.

As described above, the hydrophobic silica is then added to the lipid phase that includes the one or more hydrophobic compounds and the color pigment. Homogenization is then provided to the lipid phase comprising the hydrophobic silica. After allowing the hydrophobic silica to uniformly disperse, such as by waiting at least one minute, for example, about 5 minutes, the hydrophilic silica is added to the lipid phase that includes the hydrophobic silica.

Subsequent to adding the hydrophobic silica to the lipid phase, a hydrophilic silica is added to the lipid phase. Re-homogenization under high shear mixing is then provided to the lipid phase comprising the hydrophobic silica and the hydrophilic silica.

According to one embodiment, re-homogenization is performed directly after adding the hydrophilic silica. According to another embodiment of the invention, other particulates such as silicone elastomer are then added to the lipid phase that includes the hydrophobic silica and the hydrophilic silica. This may include adding silicone elastomer powder as well as other optional particulates such as filler particulates and particulate biological actives. After adding the silicone elastomer powder, the resulting composition may also be homogenized under high shear mixing. According to other embodiments silicone elastomer gel may then be added.

While in the process described above various homogenization under high shear mixing steps are described, these steps need not be discrete (stopping and re-starting). The homogenization under high shear mixing may, according to certain embodiments, be provided continuously, such as by beginning during or just after addition of the initial particulate and not stopping until after the last portion of particulate is added. According to one embodiment, after the last portion of particulate is added, homogenization under high shear mixing is stopped, silicone elastomer gel is added, homogenization is then restarted and continued for a period of time such as five minutes or more.

Compositions made by the methods of the present invention are surprisingly phase stable. For example, compositions made by the methods of the present invention may be tested according to an Elevated Temperature Stability Test, wherein a sample of the composition is placed at 50° C. for a period of 13 weeks, allowed to cool to ambient temperature and visually evaluated for exudates and phase separation. Similarly, the compositions may be evaluated according to a Room Temperature Stability Test, wherein the compositions are held at 25° C. for 13 weeks and then visually evaluated for exudates and phase separation. According to certain embodiments, compositions made by the methods of the present invention pass one or both tests by showing no visual evidence of exudates or phase separation.

The following non-limiting examples further illustrate the invention.

EXAMPLES

Eight compositions, two inventive examples (Inventive Examples E1 and E2) and six comparative examples (Comparative Examples C1, C2, C3, C4, C5 and C6), were prepared. The eight compositions used identical ingredients and concentrations, as shown in Table 1, but were each prepared according to different methods. Inventive examples Ex. 1 and Ex. 2 as well as Comparative Examples C1-C6 included more than 50% oil, more than 20% particulate, and more than 10% silicone elastomer.

Inventive Example E1 was prepared using the following method: a lipid phase was prepared by combining C12-C15 alkyl benzoate, Vitamin E acetate, phenoxyethanol, organic UV-filters, *Butyrospermum parkii* butter, hydrogeneated polycyclopentadiene/isododecane, and phenylethyl resorcinol and mixing under low shear (500 rpm or less). The lipid phase was heated to about 90° C. and held for five minutes to melt all solid material. The lipid phase was cooled and the color pigment dispersions were added at about 40 C, under low shear.

Hydrophobic silica was added and homogenized under high shear mixing was performed at 7000 rpm. After the hydrophobic silica was allowed to uniformly mix, hydrophilic silica was added and homogenized under high shear mixing at 7000 rpm. The silicone elastomer powders were added and homogenized under high shear mixing at 7000 rpm and lastly silicone elastomer gel was added and the entire composition was homogenized under high shear mixing at 7000 rpm. Inventive Example E1 was tested according to the Elevated Temperature Stability Test and the Room Temperature Stability Test and passed both—no phase instability or exudation was observed in either test.

Inventive Example E2 was prepared using a method that was identical to Inventive Example E1, except that after adding the silicone elastomer gel, the entire composition was homogenized under high shear mixing at 7000 rpm for an additional five minutes. Inventive Example E1 was tested according to the Elevated Temperature Stability Test and the Room Temperature Stability Test and passed both—no phase instability or exudation was observed in either test.

Comparative Example C1 was prepared using a method that was identical to Inventive Example E1, except that low shear mixing at 500 rpm was used at all stages in the process. Comparative Example C1 was tested according to the Elevated Temperature Stability Test and the Room Temperature Stability Test and passed the Room Temperature Stability Test, but failed the Elevated Temperature Stability Test. In the latter, phase instability or exudation was observed.

Comparative Example C2 was prepared using a method that was identical to Comparative Example C1, except that after adding the silicone elastomer gel, the entire composition was homogenized under high shear mixing at 7000 rpm for an additional five minutes. Comparative Example C2 was tested according to the Elevated Temperature Stability Test and the Room Temperature Stability Test and failed both the Room Temperature Stability Test and the Elevated Temperature Stability Test—phase instability or exudation were observed.

Comparative Example C3 was prepared using a method that was identical to Inventive Example E1, except that the order of addition of the hydrophobic silica and the hydrophilic silica was reversed (i.e., the hydrophilic silica was added before the hydrophobic silica). Comparative Example C3 was tested according to the Elevated Temperature Stability Test and the Room Temperature Stability Test and passed both—no phase instability or exudation was observed in either test.

Comparative Example C4 was prepared using a method that was identical to Inventive Example E2, except that the order of addition of the hydrophobic silica and the hydrophilic silica was reversed (i.e., the hydrophilic silica was added before the hydrophobic silica). Comparative Example C4 was tested according to the Elevated Temperature Stability Test and the Room Temperature Stability Test and failed both the Room Temperature Stability Test and the Elevated Temperature Stability Test—phase instability or exudation were observed.

Comparative Example C5 was prepared using a method that was identical to Comparative Example C1, except that the order of addition of the hydrophobic silica and the hydrophilic silica was reversed (i.e., the hydrophilic silica was added before the hydrophobic silica). Comparative Example C5 was tested according to the Elevated Temperature Stability Test and the Room Temperature Stability Test and failed both the Room Temperature Stability Test and the Elevated Temperature Stability Test—phase instability or exudation were observed.

Comparative Example C6 was prepared using a method that was identical to Comparative Example C2, except that the order of addition of the hydrophobic silica and the hydrophilic silica was reversed (i.e., the hydrophilic silica was added before the hydrophobic silica). Comparative Example C6 was tested according to the Elevated Temperature Stability Test and the Room Temperature Stability Test and failed both the Room Temperature Stability Test and the Elevated Temperature Stability Test—phase instability or exudation were observed.

The results of the stability testing shows that by adding the hydrophobic silica followed by adding the hydrophilic silica and using high shear (as in Inventive Examples E1 and E2) rather than low shear (as in Comparative Example C1), phase stability is obtained. Adjusting the process of Comparative Example C1 to incorporate high shear at the end of the process (as in Comparative Example C2) does not create a phase stable product.

Furthermore, when hydrophilic silica is added before the hydrophobic silica (as in Comparative Examples C3-C6), stability is poor. The exception in the case where high shear is used during the process, but not at the end (Comparative Example C3), which passed stability testing. This appears to show that adding hydrophilic silica prior to hydrophobic silica is at best highly process sensitive, and should be avoided to reduce the risk of stability failures. On the contrary, by adding the hydrophobic silica before the hydrophilic silica and, as described, providing homogenization under high shear mixing during the process, stability is surprisingly provided.

TABLE 1

| Ingredient | Components | Wt. % |
|---|---|---|
| Silicone elastomer gels | Isododecane; Dimethicone/Bis-Isobutyl PPG-20 Crosspolymer; Dimethicone; Cetearyl Dimethicone | 39% |
| Organic UV-filters | Bemotrizinol; ethylhexyl methoxycinnamate; ethylhexyl triazone; DHHB; | 13.5% |
| Oil | C12-C15 alkyl benzoate | 5.5% |
| Film-forming polymer in oil | Hydrogeneated polycyclopentadiene; isododecane | 5% |
| Wax | Butyrospermum parkii butter | 0.5% |
| Color pigment dispersion in oil | Iron oxide in oils and dispersant | 1.908% |
| Filler pigment dispersion in oil | Titanium dioxide in oils and dispersant | 18.28% |
| Preservative | Phenoxyethanol | 0.7 |
| Vitamin | Vitamin E Acetate | 0.25 |
| Silicone elastomer powder | Dithicone/Vinyl dimethicone crosspolymer | 5% |
| Hydrophobic silica | silica dimethyl silylate | 2% |
| Hydrophilic silica | silica | 0.4% |
| Biological active | Phenylethyl resorcinol | 0.4% |
| Filler particulate | Mica | 2.51% |
| Biological active | Ascorbic acid | 5% |
|  |  | 99.948% |
| TOTAL |  | 100.0 |

We claim:

1. A method of making an anhydrous, pigmented sunscreen composition, comprising in sequence:
   adding a hydrophobic silica to a lipid phase comprising a dispersed color pigment and an organic UV-filter;
   homogenizing the lipid phase comprising the hydrophobic silica by rotary mixing at a rotation speed of at least 1000 rpm;
   adding a hydrophilic silica to the lipid phase comprising hydrophobic silica; and
   re-homogenizing the lipid phase comprising the hydrophobic silica and the hydrophilic silica by rotary mixing at a rotation speed of at least 1000 rpm.

2. The method of claim 1, wherein said homogenizing step is performed for at least one minute.

3. The method of claim 1 further comprising adding a silicone elastomer after said re-homogenizing step.

4. The method of claim 3, wherein the amount of silicone elastomer added is 8% by weight of the composition.

5. The method of claim 1, wherein said anhydrous, pigmented sunscreen composition comprises about 40% to about 75% by weight of oil.

6. The method of claim 3, wherein the anhydrous, pigmented sunscreen composition comprises about 1% by weight of waxes.

\* \* \* \* \*